(12) United States Patent
Ansari et al.

(10) Patent No.: US 6,670,472 B2
(45) Date of Patent: Dec. 30, 2003

(54) PROCESS FOR THE PREPARATION OF 10-METHOXYCARBAMAZEPINE

(75) Inventors: Shahid Akhtar Ansari, Karnataka (IN); Ravindra Bhat, Karnataka (IN); Ashok Krishna Kulkarni, Karnataka (IN)

(73) Assignee: Max India Limited (IN)

( * ) Notice: Subject to any disclaimer, the term of this patent is extended or adjusted under 35 U.S.C. 154(b) by 0 days.

(21) Appl. No.: 10/269,084

(22) Filed: Oct. 9, 2002

(65) Prior Publication Data

US 2003/0105076 A1 Jun. 5, 2003

(30) Foreign Application Priority Data

Oct. 9, 2001 (EP) .............................................. 01308631

(51) Int. Cl.⁷ ........................................... C07D 223/22
(52) U.S. Cl. ........................................................ 540/589
(58) Field of Search .......................................... 540/589

(56) References Cited

FOREIGN PATENT DOCUMENTS

| WO | WO 96/21649 | 7/1996 |
|---|---|---|
| WO | WO 01/56992 | 8/2001 |

*Primary Examiner*—Bruck Kifle
(74) *Attorney, Agent, or Firm*—Sheridan Ross, P.C.

(57) ABSTRACT

A process for the preparation of 10-methoxycarbamazepine, an important intermediate in the preparation of 10-oxo-10,11-dihydro-5H-dibenz(b,f)azepine-5-carboxamide (oxcarbazepine) from 10-methoxy-5H-dibenz(b,f)azepine (10-methoxyiminostilbene), is disclosed, which process comprises reacting 10-methoxyiminostilbene with cyanic acid (HOCN) in the presence of a mild acidic reagent in a solvent. Also disclosed is an improved method for the hydrolysis of 10-methoxycarbamazepine to oxcarbazepine, which method comprises carrying out the hydrolysis in a biphasic system chosen such that the oxcarbazepine is substantially insoluble in both phases, whereas the by-products or impurities are soluble in at least one of the phases. The oxcarbazepine thereby prepared is an anticonvulsant, and has been proposed for use as an anti-epileptical agent in the treatment of AIDS-related neural disorders, and for the treatment of Parkinson's disease and/or Parkinsonian syndromes.

23 Claims, No Drawings

PROCESS FOR THE PREPARATION OF 10-METHOXYCARBAMAZEPINE

The present invention relates to an improved process for preparing 10-methoxycarbamazepine (10-methoxy-5H-dibenz(b,f)azepin-5-carboxamide), an important intermediate in the preparation of 10-oxo-10,11-dihydro-5H-dibenz(b,f)azepine-5-carbaxamide (oxcarbazepine) from 10-methoxy-5H-dibenz(b,f)azepine (10-methoxyiminostilbene).

Oxcarbazepine is an anticonvulsant drug (as described in U.S. Pat. No. 3,642,775), and has been proposed for use as an anti-epileptical agent in the treatment of AIDS-related neural disorders (as described in PCT patent specification no. WO 94/20110); and for the treatment of Parkinson's disease and/or Parkinsonian syndromes (as described in U.S. Pat. No. 5,658,900 and European patent specification no. 678 026).

Various processes for preparing oxcarbazepine have been described in the prior art. For example, U.S. Pat. No. 3,642,775 describes the preparation of oxcarbazepine from 10-methoxyiminostilbene (Scheme-1), which is first phosgenated in toluene, followed by amidation (ethanol and ammonia) and hydrolysis in an acidic medium to furnish the desired product. The main drawback of this process is the use of phosgene ($COCl_2$), a toxic and hazardous substance.

Canadian patent specification no. 1 112 241 describes an alternative preparation of oxcarbazepine from the catalysed re-arrangement of 10,11-epoxycarbamazepine, which itself may be prepared from carbamazepine by reaction with m-chloroperbenzoic acid (CPBA) (Scheme-2). However, the drawbacks of this process are: use of carbamazepine, an expensive raw material; and converting this into its corresponding epoxide in poor yields and quality.

SCHEME - 1

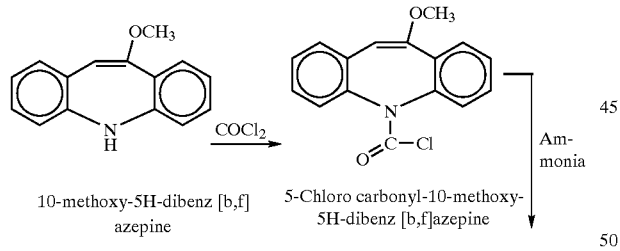

10-methoxy-5H-dibenz [b,f]azepine → 5-Chloro carbonyl-10-methoxy-5H-dibenz [b,f]azepine

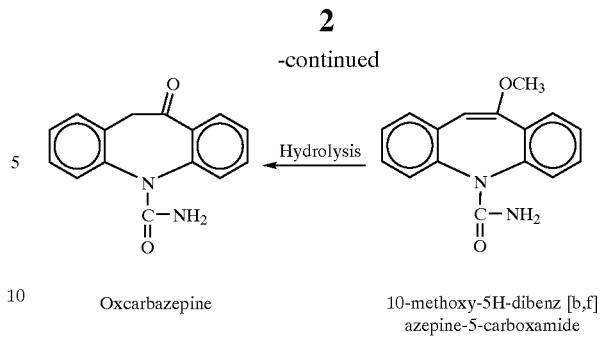

Oxcarbazepine ← 10-methoxy-5H-dibenz [b,f]azepine-5-carboxamide

SCHEME - 2

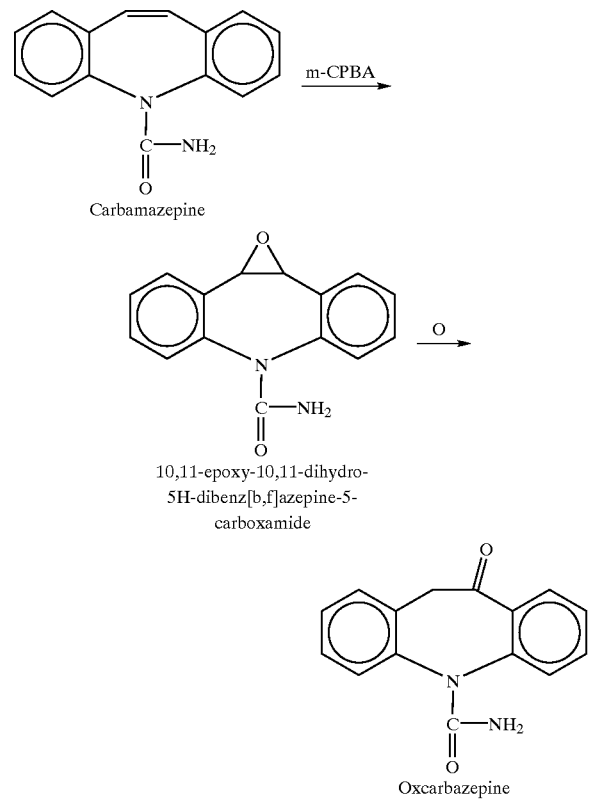

Carbamazepine → 10,11-epoxy-10,11-dihydro-5H-dibenz[b,f]azepine-5-carboxamide → Oxcarbazepine Another process, disclosed in European patent specification no. 028 028, starts from 5-cyanoiminostilbene through nitration, reduction and hydrolysis stages (Scheme-3). However, the drawback of the process is in the preparation of the 5-cyanoiminostilbene itself, which can be made from iminostilbene and cyanogen chloride. The latter is also toxic, hazardous and difficult to handle.

SCHEME - 3

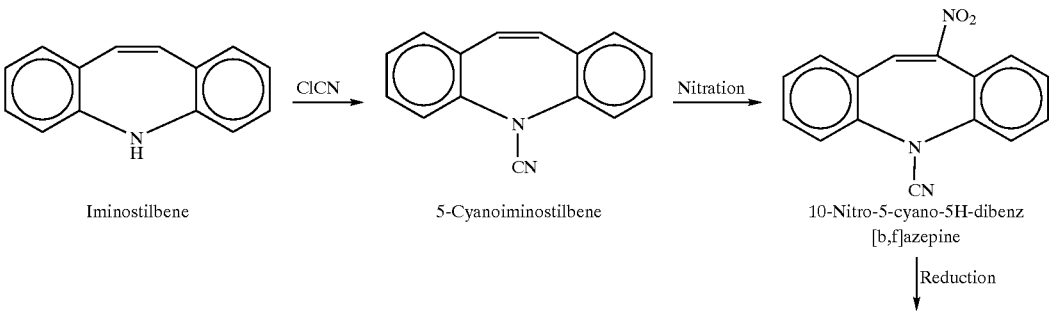

Iminostilbene → 5-Cyanoiminostilbene → 10-Nitro-5-cyano-5H-dibenz[b,f]azepine

Reduction

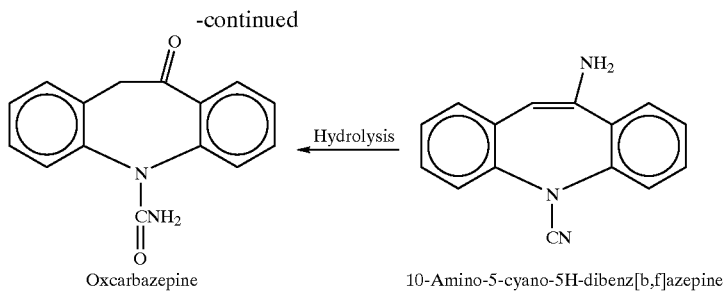

Oxcarbazepine ← Hydrolysis ← 10-Amino-5-cyano-5H-dibenz[b,f]azepine

Another alternative is described in Swiss patent specification no. 642 950 and comprises hydrolysis, using concentrated sulphuric acid, of the corresponding chloride (10-chloro-5H-dibenz[b,f]azepin-5carboxamide) to form the oxcarbazepine.

More recently, a process has been described in PCT patent specification no. WO 96/21649 (Scheme-4), which starts with 10-methoxyiminostilbene and treats it with an alkali or alkaline earth metal cyanate and acid to produce 10-methoxycarbamazepine which, on acid hydrolysis, furnishes oxcarbazepine. Alternatively, 10-methoxyiminostilbene is first hydrolysed to produce 10-oxo-iminodibenzyl (10-keto-iminodibenzyl) which, upon condensation with chlorosulphonyl isocyanate followed by hydrolysis, furnishes oxcarbazepine. Chlorosulphonyl isocyanate is a very costly, highly moisture-sensitive and toxic reagents which is the main drawback of this latter process.

The biggest problem with the former process is that 10-methoxyiminostilbene undergoes two kinds of competitive reactions when an alkali metal cyanate and an acid are added. The enol-ether moiety of the compound undergoes hydrolysis to give the corresponding ketone ("oxo" compound), which does not undergo a carboxamidation reaction with HOCN, whereas the imino function of the intact 10-methoxyiminostilbene does undergo a carboxamidation reaction. Therefore, the end result is that a mixture of oxcarbazepine, oxo-iminodibenzyl and impurities are obtained, after hydrolysis, making the subsequent crystallization process highly tedious and uneconomical.

SCHEME - 4

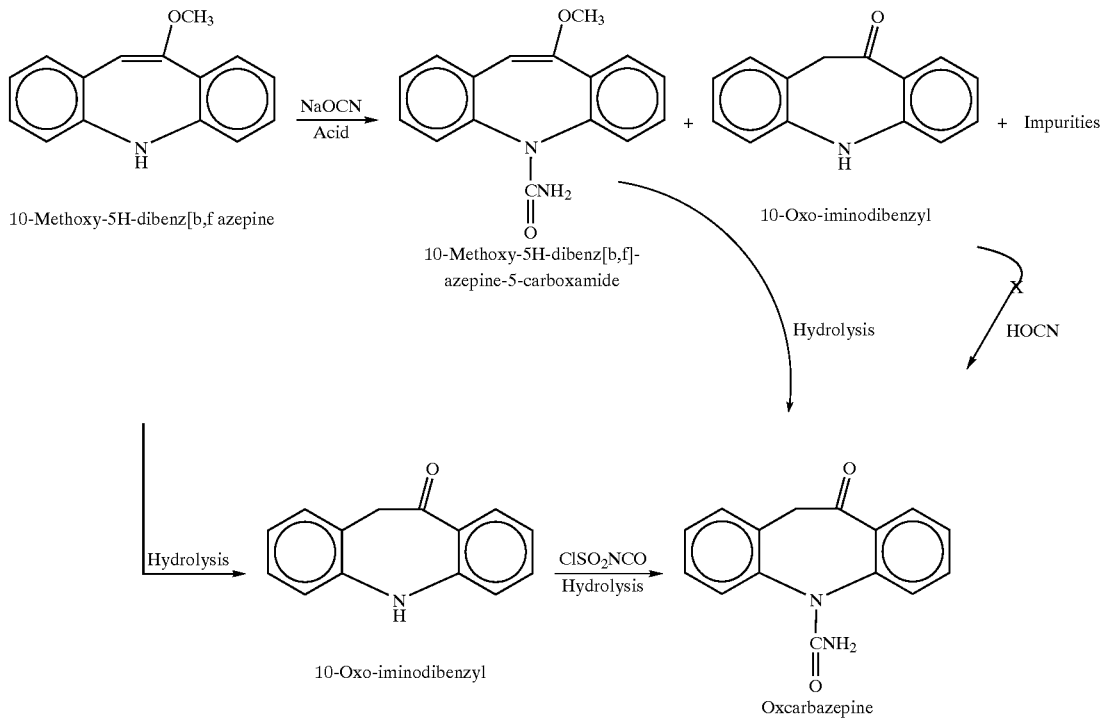

The acids that are used in this reaction (Scheme-4), according to the Examples of WO 96/21649, include acetic acid, mono-, di- and tri-chloroacetic acids, dry HCl and concentrated sulphuric acid etc. The general description teaches that concentrated mineral acids are to be used, optionally in solution in the organic acids. Nevertheless, all these acids produce substantial quantities of side products, ie oxo-iminodibenzyl and impurities formed therefrom. Due to this, although the conversion is high, the selectivity leading to the carboxamidation reaction is poor.

Furthermore, international patent specification no. WO 01/56992 describes the use of acetic acid in the absence of an additional solvent in this process, which is stated to result in an improved yield. Nothing about the purity of the end-product (oxcarbazepine) is mentioned, however, and the specific example given shows that the yield thereof is less than or equal to 78% after hydrolysis with water and sulphuric acid in the absence of a solvent such as toluene.

All the known methods therefore suffer from disadvantages, in particular, the requirement to use "environmentally unfriendly" reactants, and/or result in poor yields due to side reactions as mentioned above. In particular, the method described in WO 01/56992 precludes the use of a solvent, which imposes unfavourable limitations on the subsequent processing of the intermediate in the preparation of the end-product.

We have surprisingly found that reaction of 10-methoxyiminostilbene with cyanic acid (HOCN) in the presence of a mild acidic reagent, especially an aromatic acid, enables the disadvantages of the prior art preparation of 10-methoxycarbamazepine to be overcome. In particular, it allows for the use of a solvent in the subsequent reaction steps, which has advantages as will be further described hereinbelow Accordingly, the present invention provides a process for the preparation of 10-methoxycarbamazepine, which process comprises reacting 10-methoxyiminostilbene with HOCN in a solvent therefor in the presence of a mild acidic reagent. It is important that the mild acidic reagent be chosen so that the enol-ether function is not rapidly hydrolysed. Accordingly, this reagent is preferably a weak acid, such as an aromatic acid. Preferred aromatic acids include weak, non-aliphatic organic acids, such as benzoic acid and substituted benzoic acids; suitable substituents being halo, especially chloro eg para-chlorobenzoic acid. Suitably, the acid has a pKa value in the range of from about $10^{-4}$ to $10^{-5}$.

Furthermore, the mild acidic reagent is preferably relatively insoluble in the solvent, especially at room temperature but also preferably at the temperature of the reaction, compared to other acids, such as acetic acid. Suitably, the mild acidic reagent has a solubility in the solvent of less than 75%, preferably less than 50% and more preferably less than 25% in the solvent. Especially preferred is when the mild acidic reagent has a solubility of less than about 10–12%, even at elevated temperatures, such as at the temperature of the reaction, and particularly preferred is when the mild acidic reagent has a solubility of less than about 1% at room/ambient Temperature. In this context, it is to be understood that 'room temperature' is less than 35° C. and more usually about 20–25° C., such as 21–22° C. Of all the aromatic acids, benzoic acid is the most suitable acid in terms of selectivity (by 'selectivity' in this context is meant preference for the carboxamidation reaction over the enol-ether hydrolysis).

Excess molar quantity of the weak acid is preferably used in comparison to the 10-methoxyiminostilbene starting material; for example, in the range of from 2 to 10 molar excess, more preferably about 5 to 8 times, eg 6–7 times, benzoic acid is most preferably employed in the reaction. Most of the acidic reagent can be easily recovered and re-used, such as up to 90–95% can be re-cycled. Such acids less readily hydrolyse the enol-ether moiety present in the 10-methoxyiminostilbene, while nevertheless being able readily to catalyse the reaction between the 10-methoxyiminostilbene and the HOCN.

In another aspect, the present invention provides a process for the preparation of 10-methoxycarbamazepine, which process comprises reacting 10-methoxyiminostilbene with HOCN in the absence of a strong acid. In particular, the present invention provides a process for the preparation of 10-methoxycarbamazepine, which process comprises reacting 10-methoxyiminostilbene with HOCN in the absence of an acid having a high solubility in the solvent. In this context, a strong acid is one that would rapidly hydrolyse the enol-ether function of the starting material, such as aliphatic organic acids (including acetic acid, which also has a high solubility in solvents such as toluene) and mineral acids. For example, when aliphatic acids, such as acetic acid, monochloro-acetic acid, ethylhexanoic acid and phenylacetic acid etc, were used in the reaction, the percentage formation of 10-methoxycarbamazepine was very poor, varying from 26% to 51%. Worse still, when mineral acids, such as hydrochloric acid and sulphuric acid, were tried, the percentage formation of 10-methoxycarbamazepine was even more poor (~1%). In all the above reactions (ie when aliphatic acids or mineral acids were used), a significant percentage of 10-oxo-iminostilbene and impurities were formed. Table 1 below shows the results, using sodium cyanate in all reactions and 10 volumes of toluene per part of 10-methoxyiminostilbene.

TABLE 1

| Acid used | Reflux (hours) | Conversion (%) | HPLC Analysis ||||
|---|---|---|---|---|---|---|
| | | | % of 10-methoxycarba-mazepine | % of Oxo-IDB | Total Impurity | % of Unreacted 10-methoxy ISB |
| Hydrochloric acid | 4 | 89.63 | 0.24 | 70.19 | 19.19 | 10.37 |
| Sulphuric acid | 4 | 99.48 | 1.12 | 93.67 | 4.69 | 0.52 |
| Acetic acid | 12 | 59.05 | 26.22 | 12.97 | 19.86 | 40.95 |
| Monochloro-acetic acid | 12 | 96.32 | 51.5 | 24.00 | 20.82 | 3.68 |
| Ethylhexanoic acid | 22 | 44.14 | 22.86 | 12.93 | 8.35 | 55.86 |
| Benzoic acid | 12 | 98.00 | 75.50 | 9.10 | 13.40 | 2.00 |
| p-Chlorobenzoic acid | 12 | 99.66 | 56.44 | 20.00 | 23.22 | 0.34 |
| o-Chlorobenzoic acid | 12 | 98.13 | 31.25 | 54.77 | 12.11 | 1.87 |
| 2,4-Dichlorobenzoic acid | 6 | 98.48 | 55.45 | 30.04 | 12.99 | 1.52 |
| Phenylacetic acid | 6 | 72.88 | 34.38 | 18.36 | 20.14 | 27.12 |

On the contrary, when the aromatic acids such as mentioned above are used, the selectivity of the main reaction (ie the carboxamidation reaction as compared to hydrolysis of the enol-ether moiety) can increase to more than 75%. This results in improved efficiency and eventually in simpler methods of purification of the end product oxcarbazepine, resulting in easier commercialization of the process.

The carboxamidation of the 10-methoxyiminostilbene according to the present invention is preferably carried out in an organic medium, most preferably under reflux conditions. The organic medium is suitably an aromatic hydrocarbon solvent or an aliphatic chlorinated solvent, such as benzene, toluene, xylene, dichloromethane, chloroform and dichloroethane etc, including others described in relation to the Scheme-4 synthesis mentioned above and in WO 96/21649. The solvent(s) used in the carboxamidation reaction also play an important role in the selectivity and completion of reaction. We have found that toluene is the best solvent both in terms of selectivity and completion of reaction. It is important that the solvent is chosen such that the starting material and the HOCN are both soluble therein. Furthermore, as indicated above, it is important that the weak acid is relatively insoluble therein.

The HOCN reacts with the imino function to produce desired intermediate, 10-methoxycarbamazepine, which can afford the pharmacologically active end-product, ie oxcarbazepine, after hydrolysis.

The HOCN may be generated in situ by reaction of an alkali metal cyanate with the mild acidic reagent. Suitable cyanates include sodium and potassium, preferably sodium, cyanates. However, other methods of generating the HOCN, such as from cyanuric acid (as described in the Merck Index or by Linhard in Anorg Allgem Chem 236 200 (1938)) or other means may be used. Nevertheless, we have found that the method using sodium cyanate and an aromatic organic acid, especially benzoic acid, is commercially the most viable. In the preferred method of this invention, therefore, the mild acidic reagent is also capable of reacting with an alkali metal cyanate to produce cyanic acid (HOCN).

Accordingly, the present invention in a preferred aspect provides a process for the preparation of 10-methoxycarbamazepine, which process comprises reacting 10-methoxyiminostilbene with an alkali metal cyanate and a mild acidic reagent, as defined above.

Accordingly, the present invention further provides an improved method for preparing oxcarbazepine from 10-methoxystilbene, wherein the improvement comprises preparing the intermediate 10-methoxycarbamazepine according to the method described above.

The intermediate 10-methoxycarbamazepine is then preferably hydrolysed with an acid, more preferably a dilute mineral acid, such as hydrochloric and sulphuric acids, especially hydrochloric acid (HCl) to furnish oxcarbazepine. Finally, the oxcarbazepine thus obtained may be purified in a mixture of solvent systems selected from both a protic solvent with either an aromatic hydrocarbon solvent or a halogenated aliphatic solvent and an aromatic hydrocarbon solvent with a halogenated aliphatic solvent. Preferably, the mixed solvent system is one wherein the oxcarbazepine is soluble at elevated temperatures, suitably in the range of from 45 to 75° C., but crystallizes therefrom upon cooling. The oxcarbazepine may not be appreciably soluble in any of these solvents individually, but may be soluble in the mixture at elevated temperature. Examples of suitable mixtures include those such as methanol:toluene; dichloromethane:toluene; dichloroethane:toluene; dichloromethane:methanol; and dichloroethane:methanol.

Hydrolysis of the methoxycarbamazepine is preferably carried out in a biphasic system chosen such that the oxcarbazepine is substantially insoluble in both phases, whereas the by-products or impurities are soluble in at least one of the phases. The biphasic system comprises an organic phase and an aqueous phase in which the organic phase preferably comprises the solvent used in the carboxylation reaction eg toluene. Preferably, an excess of this solvent, compared with the amount of impurity or by-product to be produced, is used in the process of this invention. The preferred aqueous phase comprises an aqueous solution of the acid for the hydrolysis step and is therefore most preferably dilute hydrochloric acid. The advantage of this biphasic system is that oxcarbazepine formed in the reaction is thrown out from both the solvents, whereas the impurities remain soluble in the toluene.

Accordingly, the present invention further provides an improved method of hydrolyzing 10-methoxycarbamazepine, which improvement comprises carrying out the hydrolysis in a biphasic system as described above.

Especially preferred is when both improved processes of the invention are used, consecutively. The improved processes of the invention enable the oxcarbazepine thereby produced to be purified in a single step.

An especially preferred method according to this invention comprises reaction of 10-methoxy-5H-dibenz[b,f]azepine with benzoic acid and sodium cyanate in toluene at reflux temperature to give 10-methoxy-5H-dibenz[b,f]azepine carboxamide as a major product (such as about 75%), along with 10-oxo-iminodibenzyl and other impurities. The reaction mixture is thereafter filtered and washed with water, and the toluene layer taken as such for hydrolysis in a biphasic system (aqueous hydrochloric acid/toluene) to furnish oxcarbazepine, which is purified just once (whereas twice at least is needed when the prior art process is carried out) in a mixture of methanol and dichloromethane (Scheme-5).

SCHEME-5

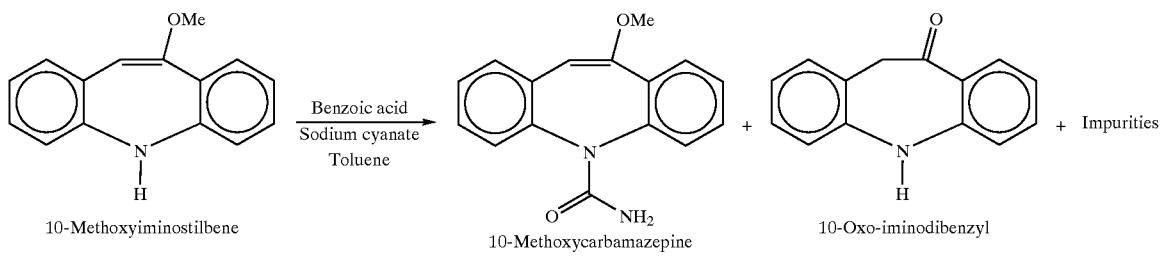

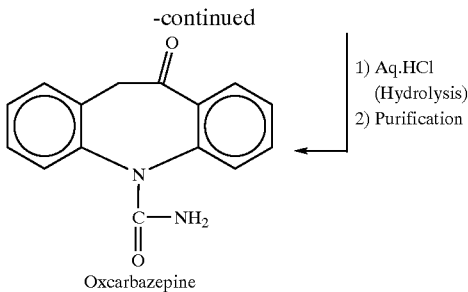

Oxcarbazepine 10-methoxyiminostilbene, the key starting material in the following Examples, maybe prepared according to the process disclosed in Belgian patent specification no. 597 793 and Swiss patent specification no. 392 515.

The following examples serve to further illustrate the present invention. In each, the oxcarbazepine end-product was determined by IR, 1H-NMR, HPLC and MP/mixed MP with respect to an authentic sample. Purity was generally determined by HPLC and found to be in excess of 99%.

COMPARATIVE EXAMPLE A

Using Monochloro-Acetic Acid and Sodium Cyanate

A mixture of 100 gms of 10-methoxyiminostilbene in 1000 mL of toluene containing 106 gms of monochloro-acetic acid and 73 gms of sodium cyanate were heated to 40° C. under stirring and maintained for 4 hours. After completion of the reaction (monitored by HPLC and/or TLC), the mixture was cooled to room temperature, filtered and washed with 5% sodium carbonate solution followed by water. The toluene layer was then added to 1000 mL of 2N hydrochloric acid, and the mixture was heated to 75–80° C. and maintained for 2 hours under good agitation. It was then cooled to 0–5° C. and maintained for 2 hours, and the product oxcarbazepine was separated by filtration. This was then purified twice in toluene:methanol followed by methanol:dichloromethane solvent mixture to furnish 28 gms of pure oxcarbazepine.

EXAMPLE 1

Using benzoic acid and sodium cyanate

A mixture of 100 gms of 10-methoxyiminostilbene in 2000 mL of toluene containing 274 gms of benzoic acid and 370 gms of sodium cyanate were heated to reflux temperature under stirring and maintained for 12 hours. The reaction mixture was then cooled to room temperature and filtered. The clear toluene filtrate was washed with 5% sodium carbonate solution followed by water. The toluene layer was then added to 1000 mL of 2N hydrochloric acid and the mixture was heated at 75–90° C. for a period of 2 hours under good agitation. It was then cooled to 0–5° C., maintained for 2 hours and the product oxcarbazepine was separated by filtration. This was then purified once in a dichloromethane:methanol mixture to furnish 46 gms of pure oxcarbazepine. Purity was determined by HPLC to be 99.45%.

EXAMPLE 2

Using para-chlorobenzoic acid and sodium cyanate

A mixture of 100 gms of 10-methoxyiminostilbene in 1000 mL of toluene containing 351 gms of para-chlorobenzoic acid and 370 gms of sodium cyanate were heated to reflux and refluxed for 12 hours. The reaction mixture was then cooled to room temperature and filtered. The clear toluene filtrate was then washed with 5% sodium carbonate solution followed by water. The toluene layer was then added to 1000 mL of 2N hydrochloric acid and the mixture was heated at 75–80° C. for a period of 2 hours under good agitation. It was then cooled to 0–5° C., maintained for 2 hours and the product oxcarbazepine was separated by filtration. This was then purified once in a dichloromethane methanol mixture to furnish 44 gms of pure oxcarbazepine.

EXAMPLE 3

Alternative Use of benzoic acid and sodium cyanate

The method of Example 1 was repeated, but using 1000 ml toluene; 164 g benzoic acid and 44 g of sodium cyanate, which were heated to 85–90° C. for 14 hours with the 10-methoxyiminostilbene to result in 55 gms of pure oxcarbazepine, found to be 99.45% pure by HPLC.

EXAMPLE 4

Using 2,4-dichloro benzoic acid and sodium cyanate

A mixture of 100 gms of 10-methoxyiminostilbene in 1000 mL of toluene containing 430 gms of 2,4-dichlorobenzoic acid and 370 gms of sodium cyanate were heated to reflux and refluxed for 6 hours. The reaction mixture was then cooled to room temperature and filtered. The clear toluene filtrate was then washed with 5% sodium carbonate solution followed by water. The toluene layer was then added to 1000 mL of 2N hydrochloric acid and the mixture was heated at 75–80° C. for a period of 2 hours under good agitation. It was then cooled to 0–5° C., maintained for 2 hours and the product oxcarbazepine was separated by filtration. This was then purified once in a dichloromethane:methanol mixture to furnish 40 gms of pure oxcarbazepine.

EXAMPLE 5

Using benzoic acid and potassium cyanate

The method was carried out according to that described in Example 1, but replacing sodium cyanate with potassium cyanate (461.5 gm) and reflux maintained for 24 hrs to complete consumption of starting material. Following the similar process for hydrolysis and purification produced 32.00 gm of pure oxcarbazepine. Purity was determined according to Example 1 and found 98.80%.

EXAMPLE 6

The method was carried out according to that described in Example 1, but replacing 2N hydrochloric with 2N sulphuric acid (1000 mL). Following a similar process of carboxamidation and purification produced 25.00 gm of pure oxcarbazepine. Purity was determined according to Example 1 and found 98.50%.

EXAMPLE 7

Hydrolysis Step Using 2N monochloro-acetic acid

The method was carried out according to that described in Example 1, but replacing 2N hydrochloric acid with 2N monochloro-acetic acid (1000 mL). The reaction mixture was heated to 75° C. to 80° C. and maintained for 24 hrs (after which 20% of unreacted methoxy ISB was found to be present). Under similar conditions for the carboxamidation reaction and purification step, this comparative Example produced 20.00 gm of pure oxcarbazepine. Purity was determined according to Example 1 and found to be 98.00%.

EXAMPLE 8

Purification Using toluene:methanol solvent system

The method was carried out according to that described in Example 1, but replacing dichloromethane with toluene. Following a similar process of carboxamidation and hydrolysis produced 47.0 gm of pure oxcarbazepine. Purity was determined according to Example 1 and found 98.50%.

EXAMPLE 9

Purification Using toluene:dichloromethane solvent system

The method was carried out according to that described in Example 1, but replacing methanol with toluene. Following a similar process of carboxamidation and hydrolysis produced 45.00 gm of pure oxcarbazepine. Purity was determined according to Example 1 and found to be 98.00%.

What is claimed is:

1. A process for the preparation of 10-methoxycarbamazepine, which process comprises reacting 10-methoxyiminostilbene with cyanic acid (HOCN), generated in situ by reaction of an alkali metal cyanate with a mild acidic reagent, in a solvent therefore, wherein the mild acidic reagent is an aromatic acid.

2. A process according to claim 1, wherein the mild aromatic acid has a pKa value in the order of a range from $10^{-4}$ to $10^{-4}$.

3. A process according to claim 1, wherein the mild aromatic acid is benzoic acid.

4. A process according to claim 1, wherein excess molar quantity of the mild aromatic acid is used in comparison to the quantity of 10-methoximinostilbene.

5. A process according to claim 1, wherein the range of from 2 to 10 times the molar quantity of the mild aromatic acid is used in comparison to that of the 10-methoxyiminostilbene.

6. A process according to claim 1, wherein the range of from 6 to 7 times the molar quantity of the mild aromatic acid is used in comparison to that of the 10-methoxyiminostilbene.

7. A process according to claim 1, wherein at least 90% of the mild aromatic acid is recycled in a subsequent reaction.

8. A process according to claim 1, wherein the reaction of the 10-methoxyiminostilbene with the HOCN is carried out in the absence of a strong acid.

9. A process according to claim 1, wherein the reaction of the 10-methoxyiminostilbene with the HOCN is carried out in aromatic hydrocarbon solvent or an aliphatic chlorinated solvent.

10. A process according to claim 1, wherein reaction of the 10-methoxyiminostilbene with the HOCN is carried out in a solvent selected from benzene, toluene, xylene, dichloromethane, chloroform and dichloroethane.

11. A process according to claim 1, wherein reaction of the 10-methoxyiminostilbene with the HOCN is carried out in a toluene solvent.

12. A process according to claim 1, wherein the alkali metal cyanate is sodium and/or potassium cyanate.

13. A method for preparing oxcarbazepine from 10-methoxystilbene, wherein the intermediate 10-methoxycarbamazepine is prepared according to a method according to claim 1.

14. A method according to claim 13, wherein the intermediate 10-methoxycarbamazepine is hydrolysed with a dilute acid.

15. A method according to claim 13, wherein the intermediate 10-methoxycarbamazepine is hydrolysed with hydrochloric acid (HCI).

16. A method according to claim 13, wherein the oxcarbazepine thus obtained is purified in a mixture of solvent systems selected from both a protic solvent with either an aromatic hydrocarbon solvent or a halogenated aliphatic solvent and an aromatic hydrocarbon solvent with a halogenated aliphatic solvent.

17. A method according to claim 13, wherein the oxcarbazepine thus obtained is purified in a mixture of solvent systems selected from methanol:toluene; dichloromethane:toluene; dichloroethane:toluene; dichloromethane:methanol; and dichloroethane:methanol.

18. A method according to claim 13, wherein the intermediate 10-methoxycarbamazepine is hydrolysed to oxcarbazepine in a biphasic system chosen such that the oxcarbazepine is substantially insoluble in both phases, whereas the by-products or impurities are soluble in at least one of the phases.

19. A method according to claim 18, wherein the biphasic system comprises both organic and aqueous phases in which the organic phase comprises an aromatic hydrocarbon solvent or an aliphatic chlorinated solvent, such as benzene, toluene, xylene, dichloromethane, chloroform and dichloroethane.

20. A method according to claim 18, wherein the biphasic system comprises an aqueous phase and toluene.

21. A method according to claim 18, wherein the biphasic system comprises an organic phase and dilute hydrochloric acid (aq. HCI).

22. A method according to claim 18, wherein the oxcarbazepine thereby produced is purified in a single step.

23. A method according to claim 22, which method comprises (a) reaction of 10-methoxy-5H-dibenz[b,f]azepine with benzoic acid and sodium cyanate in toluene at the reflux temperature of the reaction mixture to produce a mixture of 10-methoxy-5H-dibenzllb,[b,f]azepine carboxamide together with 10-oxo-iminodibenzyl and other impurities: (b) filtering and washing with water the product mixture of step (a); subjecting the toluene layer thereof to hydrolysing conditions in a biphasic system (such as awueous hydrochloric acid/toluene) to furnish oxcarbazepine; and (c) purifying just once the oxcarbazepine produced in step (b) in a mixture of methanol and dichloromethane.

\* \* \* \* \*

UNITED STATES PATENT AND TRADEMARK OFFICE
CERTIFICATE OF CORRECTION

PATENT NO. : 6,670,472 B2
DATED : December 30, 2003
INVENTOR(S) : Ansari et al.

It is certified that error appears in the above-identified patent and that said Letters Patent is hereby corrected as shown below:

Column 11,
Line 45, please delete "$10^{-4}$ to $10^{-4}$" and replace with -- $10^{-4}$ to $10^{-5}$ --.

Column 12,
Line 56, please delete "10-methoxy-5H-dibenzllb,[b,f]azepine" and replace with -- 10-methoxy-5H-dibenz[b,f]azepine --.

Signed and Sealed this

Sixth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,670,472 B2  
DATED : December 30, 2003  
INVENTOR(S) : Ansari et al.

It is certified that error appears in the above-identified patent and that said Letters Patent is hereby corrected as shown below:

Column 5,
Line 40, delete "pKa" and insert -- $K^a$ --.

Column 11,
Line 44, delete "pKa" and insert -- $K^a$ --.

Column 12,
Line 62, delete "aweous" and insert -- aqueous --.

Signed and Sealed this

Eleventh Day of April, 2006

JON W. DUDAS  
*Director of the United States Patent and Trademark Office*

UNITED STATES PATENT AND TRADEMARK OFFICE
CERTIFICATE OF CORRECTION

PATENT NO. : 6,670,472 B2  Page 1 of 1
APPLICATION NO. : 10/269084
DATED : December 30, 2003
INVENTOR(S) : Ansari et al.

It is certified that error appears in the above-identified patent and that said Letters Patent is hereby corrected as shown below:

Column 5
Line 40, please delete "$K^a$" and replace with --Ka--.

Column 11
Line 44, please delete "$K^a$" and replace with --Ka--.

Signed and Sealed this

Nineteenth Day of February, 2008

JON W. DUDAS
*Director of the United States Patent and Trademark Office*